United States Patent

Saldana et al.

[11] Patent Number: 5,860,561
[45] Date of Patent: Jan. 19, 1999

[54] COTTON SWAB DISPENSER

[76] Inventors: Ronaldo R. Saldana; Robert R. Saldana; Juliet T. Saldana, all of 1910 Park Valley La., San Diego, Calif. 92114

[21] Appl. No.: 954,010

[22] Filed: Oct. 20, 1997

Related U.S. Application Data

[63] Continuation-in-part of Ser. No. 579,291, Dec. 27, 1995, abandoned.

[51] Int. Cl.⁶ .................................................... G07F 11/66
[52] U.S. Cl. ................................ 221/25; 221/72; 221/197
[58] Field of Search .................................. 221/25, 71, 72, 221/73, 197

[56] References Cited

U.S. PATENT DOCUMENTS

| | | | |
|---|---|---|---|
| 2,139,886 | 12/1938 | Drachenberg | 221/72 |
| 3,066,881 | 12/1962 | Krueger | 221/73 |
| 3,107,782 | 10/1963 | Jaroff et al. | 221/25 |
| 3,363,804 | 1/1968 | Frasier | 221/72 |

FOREIGN PATENT DOCUMENTS 0132588  5/1990  Japan ....................................... 221/25

*Primary Examiner*—H. Grant Skaggs
*Attorney, Agent, or Firm*—Gene Scott; Patent Law & Venture Group

[57] ABSTRACT

A device having means for dispensing a single swab at one time from a rolled inventory of swabs mounted on a continuous strip defines a means for unrolling the inventory and a means for detaching each swab in turn from the strip. A support roll is positioned to provide a rigid backing to the strip so that as the strip passes a chute, an upfacing edge of the chute wedges itself between the swab and the backing, thereby prying the swab from the backing and urging it into the dispensing chute. Transparent walls of the device provide visibility of the inventory.

16 Claims, 5 Drawing Sheets

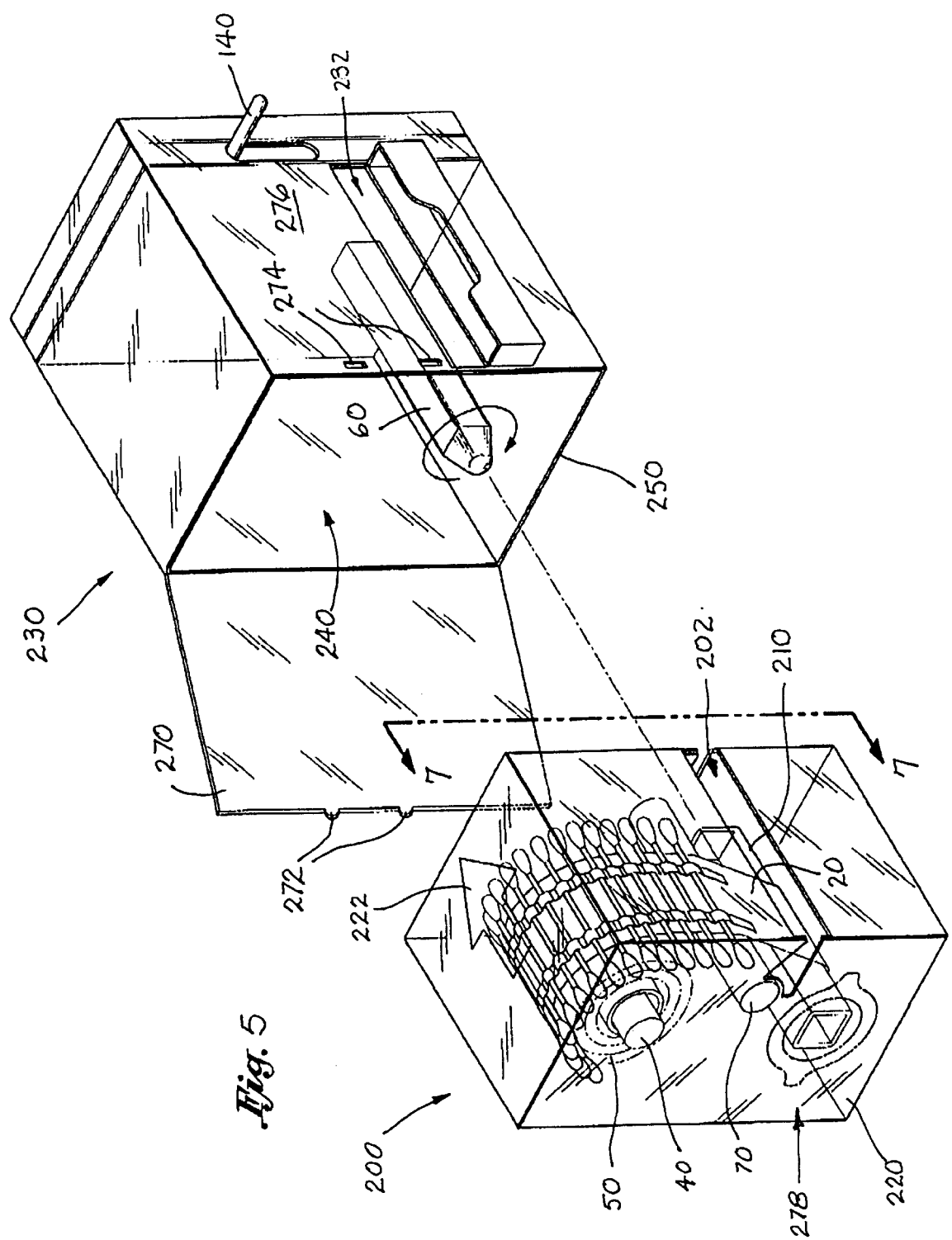

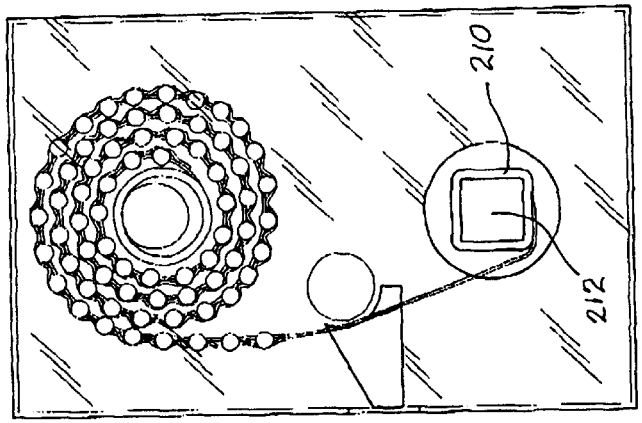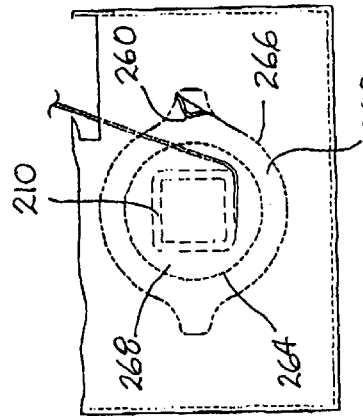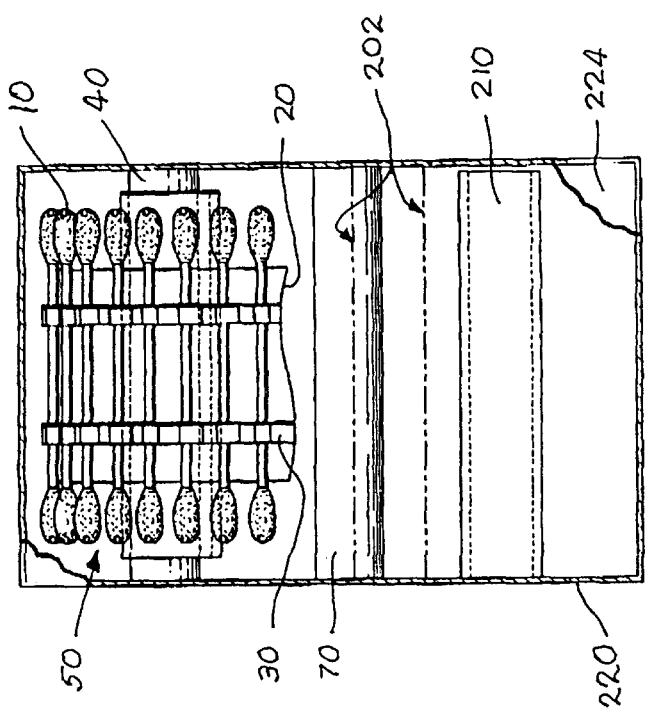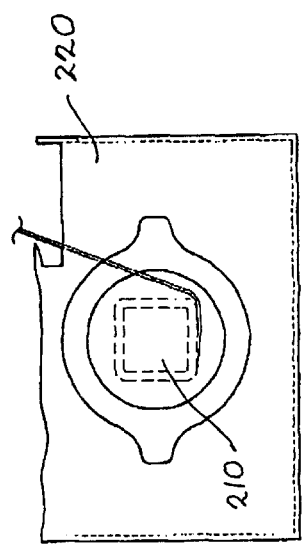

COTTON SWAB DISPENSER

This application is a continuation-in-part of prior filed application Ser. No.: 08/579,291, filed on: Dec. 27, 1995, now abandoned.

BACKGROUND OF THE INVENTION

1. Field of the Invention

This invention relates generally to dispensing devices and more particularly to an improved cotton swab dispensing device that stores and delivers cotton swabs in a sanitary manner.

2. Description of the Related Art

Invention and use of cotton swab dispensing devices is well known in the prior art.

Stawski U.S. Pat. No. 3,580,472 discloses a portable dispensing apparatus for dispensing a sterile unpacked medical swab and a moisturizing charge of a liquid medium. A package member for storing the swab as one of a plurality of stacked swabs. The package, received and supported by the apparatus, having bottom supporting structure for the swabs and both a rear cutout to allow passage of a pivotal dispensing lever and a front exit to dispense upon lever movement, the swab from the package and from an aligned dispensing slot in the apparatus.

Lemoine U.S. Pat. No. 4,989,730 discloses a plastic shipping and dispensing container for cotton swabs that has a T-section at the bottom of the container front panel that at the shipping destination is readily removed to form a dispensing opening for the cotton swabs.

However, both of the above described prior art devices provide a large holding bin in which all swabs are stored in contact with one another. While this configuration maximizes the storage capacity of the device, it is not sanitary or sterile, which is undesirable for cotton swab uses. Castner, Sr. et al. U.S. Pat. No. 4,236,637 discloses a package for marketing and vending strips of cotton swabs. The package has a cardboard backed tray like blister package with a flap on the backing covering a dispensing opening and forming a bottom for the package. While this configuration allows the swabs to be separated from one another because they are spaced apart on strips, it is still limited in that the dispenser is not refillable, thus wasting a good deal of packaging and increasing the cost of the swabs and dispenser.

Castner Sr. et al U.S. Pat. No. 4,550,857 discloses a refillable vendor or dispenser for cotton swabs releasably carried cross-wise on an elongated flexible tape wound about itself to form a roll has a plurality of mating components releasably held together to define a chamber receiving the roll for rotation about a horizontal axis. The upper portion of the chamber has a chute receiving the leading end of the roll and discharging through a slot to an external lip supporting the exposed tape from which a swab is easily picked off of the tape. A finger hole overlaying the chute provides for the pushing of the stick portions of the swabs to successively advance the tape beyond the discharge slot. The discharge slot has a severing edge to tear off that portion of the tape projecting beyond the discharge outlet.

However, both of Caster's prior art devices are limited in that they provide no means by which to automatically release swabs from the strip, thus requiring that the swabs be manually grasped by the cotton portion and manually pealed away from the strip. This procedure may result in contamination of the swab, and is therefore undesirable.

Thus there is a clear need for an improved, refillable cotton swab dispensing device that automatically dispenses swabs in an easily accessible manner so as to minimize contamination of the swab. The present invention fulfills these needs and provides further related advantages as described in the following summary.

SUMMARY OF THE INVENTION

The present invention is an improved cotton swab dispensing device that is contamination free. The device includes a dispensing spool that accepts a roll of cotton swabs packaged on a carrier strip. The roll is pulled from the dispensing spool across a support roll, to a pickup roll. A drive means rotates the pickup roll in order to pull the strip from the dispensing spool. The drive means includes a lever which is actuated once for each swab, a single swab being ejected into a receiver at the end of a chute. The lever drives a series of sprockets to rotate the pickup spool. Each swab is plucked from the carrier strip by the leading edge of the chute which is positioned against the carrier strip so that it interposes itself between each swab in turn, and the carrier strip as the strip is drawn past the leading edge on its way to the pickup spool.

Thus it is an object of the present invention to provide a cotton swab dispensing device that keeps the swabs from contacting one another or any non-sanitary surface and delivers the swabs individually in an easily accessible manner so that they may be carefully picked up without becoming contaminated in any way.

It is another object of the present invention to provide a refillable dispensing device that results in the least amount of waste, as the dispenser itself can be repeatedly refilled, the only waste produced each time is simply the strip on which the swabs are packaged. This strip may be made of a recyclable paper material.

It is yet another object of the invention to automatically release each swab from the strip before dispensing it, thus making it easier and potentially more sterile for a user to access a swab rather than necessitating that the user manually pull the swab from the strip.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention, a device for dispensing cotton swabs. In such drawings:

FIG. 5 is a perspective view of a preferred embodiment of the invention shown with a replaceable cartridge ready to be inserted into a swab dispensing case;

FIG. 6 is a front elevational view of the replaceable cartridge with a front wall thereof partially broken-away, and showing the position of an access slot, in phantom line, and also showing the internal components of the cartridge;

FIG. 7 is a right side view of the cartridge of FIG. 6 as seen from cutting plane line 7—7 shown in FIG. 5;

FIG. 8 is partial left side view of the cartridge of FIG. 6 showing the lower portion only including an attachment tab connected to an attachment ring defined by two coaxial and concentric circles of perforations and showing a portion of one end of the attachment tab in a bent position ready for tearing the tab away from the sidewall; and FIG. 9 is identical to FIG. 8 but showing the attachment tab removed.

DETAILED DESCRIPTION OF THE PREFERRED EMBODIMENT

Figure 4:
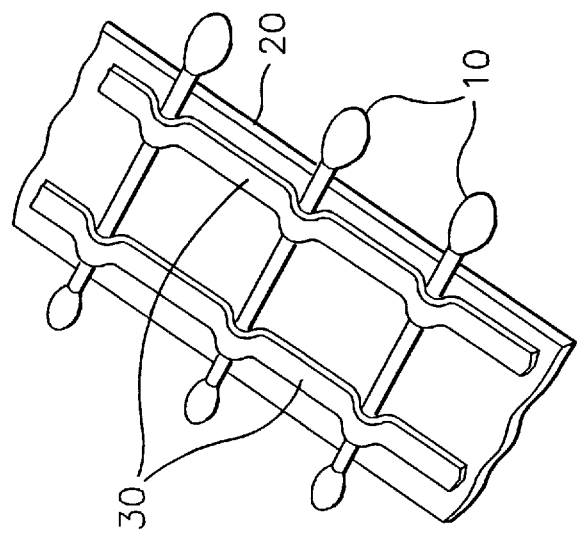
FIG. 4 is a perspective view of the carrier showing the typical arrangement of the cotton swabs and the strippable attachment means.

The above described drawing figures illustrate a device for dispensing cotton swabs 10 from a coiled inventory roll 50. The device provides storage for the inventory roll 50. The swabs 10 are carried on a flexible carrier 20 preferably made of a paper or plastic sheet stock coiled into a roll. A continuous strippable attachment means 30, preferably one or two narrow strips of paper, are adhesively laid over the swabs 10 in order to hold them against the carrier 20 and in their respective positions as the continuous roll 50 is played out during dispensing. FIG. 4 shows the preferred carrier strip 20 and the attachment means 30 for holding the swabs 10 against it. Other configurations and orientations of carriers and attachment means may be substituted for that shown in FIG. 4 within the meaning and spirit of the invention.

Figure 1B:
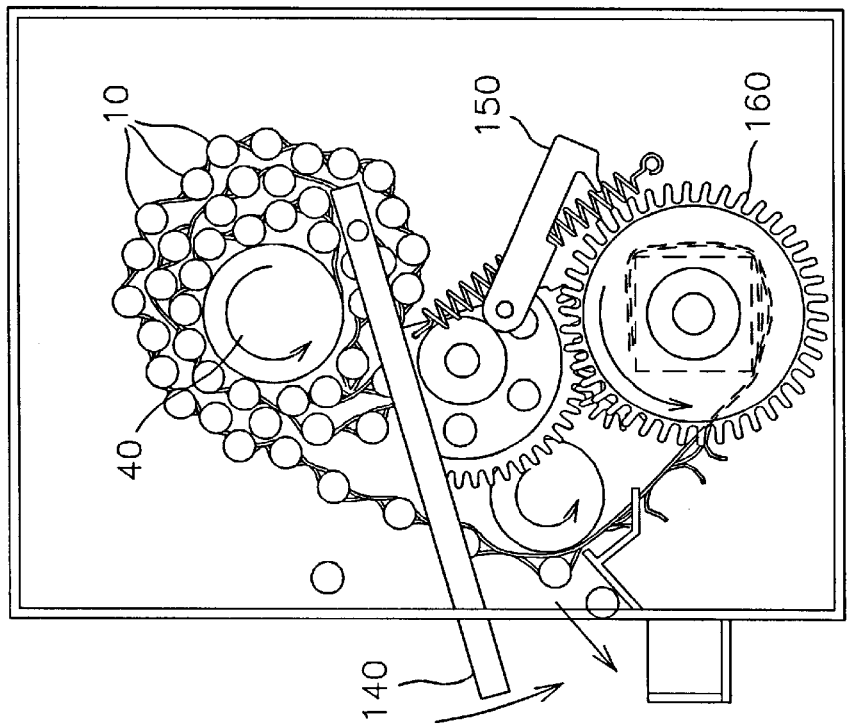
FIG. 1B is a right side elevational view thereof after dispensing a cotton swab.
Figure 1A:
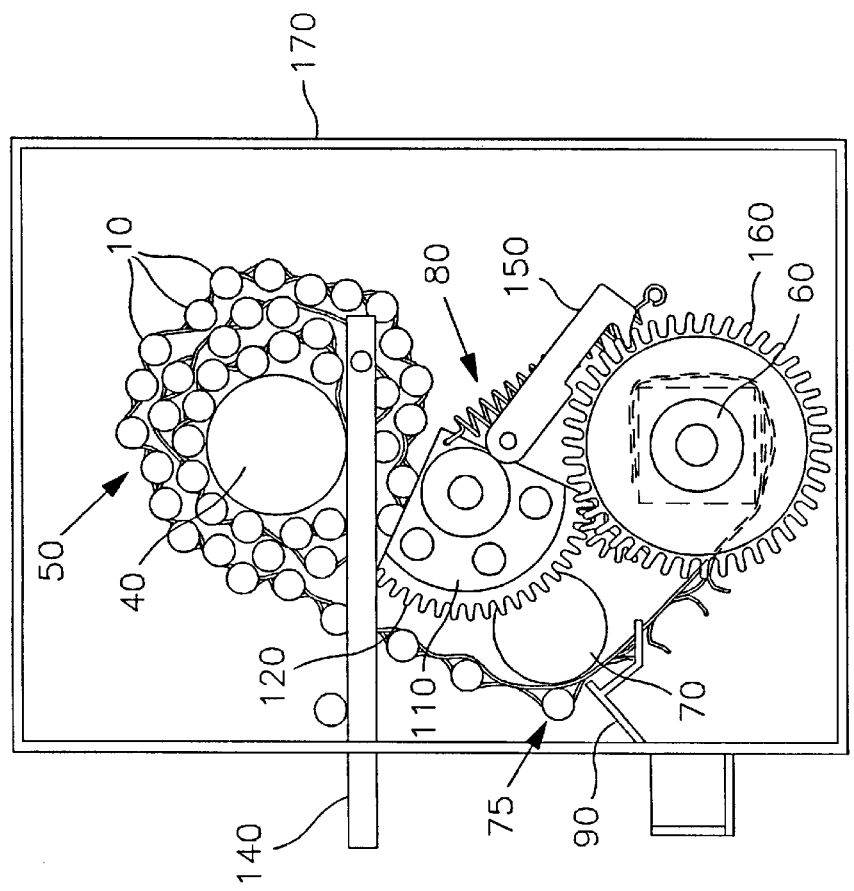
FIG. 1A is a right side elevational view of the preferred embodiment of the present invention shown in a transparent housing, prior to dispensing a cotton swab.
Figure 3:
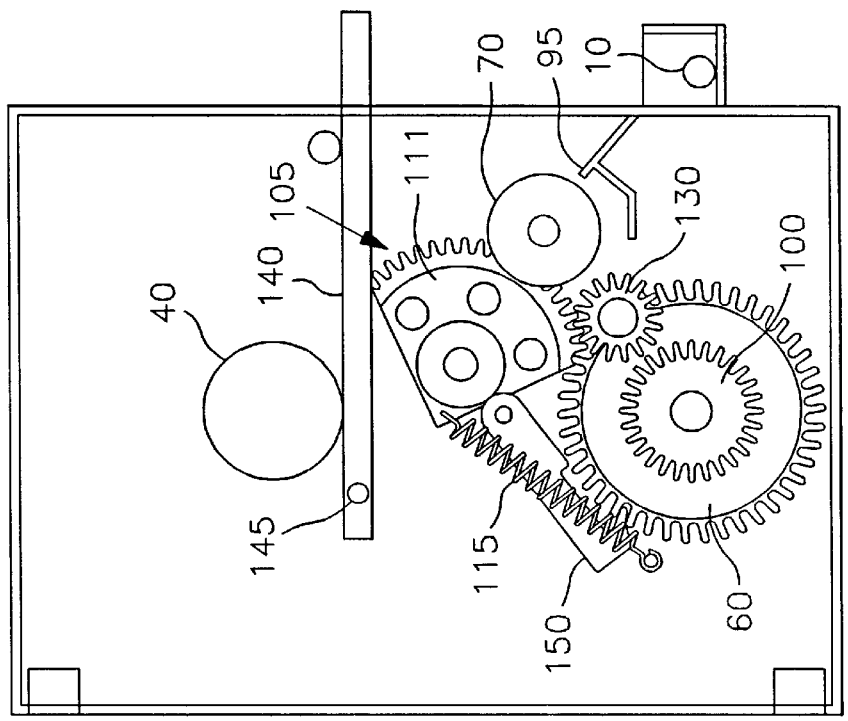
FIG. 3 is a left side elevational view thereof shown without the coiled inventory mounted on the take-up reel; the take-up reel is not shown, in order to more particularly show details of the various drive elements of the invention, and specifically showing the idler sprocket in a disengaged position as the drive sector moves back to the drive start position.
Figure 2:
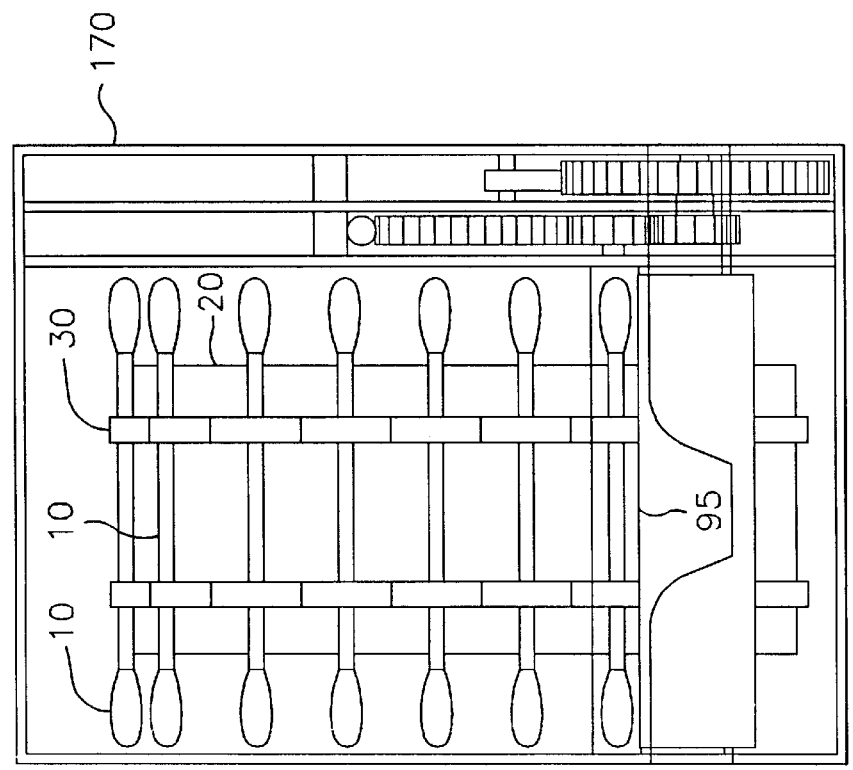
FIG. 2 is a front elevational view thereof.

The device preferably includes a storage spool 40 which may rotate or not, i.e., the coiled inventory 50 may simply rotate, sliding around on the storage spool 40, or the spool 40 itself may be rotatably mounted so as to rotate itself as well as the coiled inventory 50 during play-out. A rotating pickup spool 60 is positioned for taking up the flexible carrier 20 as the swabs are dispensed. To achieve this, the carrier 20 includes a leader portion at the beginning of each coiled inventory roll 50 which is fixed to the pickup spool 60 prior to dispensing operations. In this manner the pickup spool 60 is able to draw the carrier from the storage spool 40 as it rotates. The pickup spool 60 has a preferably square or rectangular roll as best shown in FIG. 1B, for assuring that the flexible carrier 20 does not slip on the take-up roller. A support wheel 70 is mounted as a free rotating wheel and is positioned so that the carrier 20 passes over it before being taken up on the pickup spool. As the carrier 20 passes over the support wheel 70 a portion of the carrier 20 is positioned at a swab dispensing position 75. A cotton swab stripping and dispensing chute 90 has an edge 95 positioned such that it is wedged between a cotton swab 10 in the swab dispensing position 75 and that portion of the flexible carrier 20 which is in contact with the support wheel 70. The cotton swab 10 is pulled away from the carrier 20 as the carrier moves toward the pickup spool 60, the cotton swab breaking the strippable attachment means 30, and falling into the chute 90 for dispensing. A drive means 80 rotates the pickup spool 60 thereby pulling the flexible carrier 20 from the storage spool 40 and then over the support wheel 70.

Drive means 80 may be variously configured. In the preferred embodiment, the pickup spool 60 provides radially positioned first drive tooth means 100. A drive sector 110, configured as an approximately one-forth of a fully circular sprocket, is rotatably mounted and includes outwardly extending, radially extending, second drive tooth means 105. Both the first 100, and the second 105 drive tooth means may be engaged with an idler sprocket 110 so that as the drive sector 110 is rotated from a drive start position 111, the idler sprocket 110 is rotated as well, and in turn, drives the pickup spool 60. The drive sector 110 is biased to move to the drive start position 111 by a spring 115. The idler sprocket 130 is mounted such that it engages the first 100 and the second 105 drive tooth means upon receiving driving force from the drive sector 110, and alternately, disengages itself from the first 100 and second 105 drive tooth means as the drive sector 110 moves back to the drive start position 111. This adaptation is well known in the art, so that it is not further detailed here. A drive handle 140 mounted and positioned for moving in pivotal motion pushes against the drive sector 110 in order to rotating it from the drive start position 111. A pivoted pawl 150 is positioned for engaging and alternately disengaging a toothed ratchet means 160 preferably a plurality of radially oriented teeth mounted on the pickup spool 60 such that with the pickup spool 60 rotating in a sense for taking up the carrier, the pawl, forced by the shape of its tooth 151, to disengaged the toothed ratchet means 160, and with the pickup spool 60 tending to rotate in the opposite sense, whereby the carrier 20 would play-out from the pickup spool 60, the pawl 150 engages the toothed ratchet means 160 to lock the pickup spool 60 from rotating in the opposite sense. The device is preferably enclosed within a housing 170 so that the swab inventory is maintained sanitary, the housing walls functioning to support the various parts of the drive mechanism and the spools. In the preferred embodiment at least part of the housing walls are made of a transparent material so that the swab inventory is visible.

In another preferred embodiment, shown in FIGS. 5–9, the cotton swab dispensing device includes a replaceable cartridge 200 and a swab dispensing case 230. The replaceable cartridge 200 is preferably made of paper, plastic or other cheap and disposable material and is preferably roughly cubical in shape. The replaceable cartridge 200 has an access slot 202 cut through its front surface in line with access slot 232 in case 230. As shown in FIGS. 6–7, the replaceable cartridge 200 contains the storage spool 40 which supports and plays-out the coiled inventory roll 50 of the cotton swabs 10 mounted on the flexible carrier 20. The replaceable cartridge 200 also contains the support wheel 70, which supports the flexible carrier 20 at the swab dispensing position 75. The replaceable cartridge 200 further contains a pickup spindle 210 removably mounted, as described below, onto a side wall 220 of the replaceable cartridge 200. The pickup spindle 210 is attached to the flexible carrier 20 and enables the winding up of the flexible carrier 20 as the cotton swabs 10 are dispensed. The replaceable cartridge 200 preferably contains an orienting indicia 222 such as an arrow which indicates the direction in which the replaceable cartridge 200 is oriented for insertion into the swab dispensing case 230. A front wall 224 of the replaceable cartridge 200 is preferably transparent so the storage spool 40 is visible from the outside.

The swab dispensing case 230 is preferably made of a rigid material such as plastic. As described more fully below, at least some of the material is preferably transparent. The swab dispensing case 230 provides a storage space 240 for holding the replaceable cartridge 200. The swab dispensing case 230 contains an access aperture 250 for inserting and removing the replaceable cartridge 200 into and out of the storage space 240. A front panel 276 of the swab dispensing case 230 contains a chute aperture 232 and a stripping and dispensing chute 90 (not shown in FIG. 5, for clarity), having an edge 95. The swab dispensing case 230 contains the rotating pickup spool 60 connected to the drive means 80 as described above. The rotating pickup spool 60 engages with the pickup spindle 210 when the swab dispensing case 230 is inserted into the swab dispensing case 230. In this preferred embodiment, the pickup spindle 210 defines a hollow space 212 therewithin, and the pickup spool 60 engages within the hollow space 212 of the pickup spindle 210 such that rotation of the pickup spool 60 causes the pickup spindle 210 to rotate therewith. The pickup spindle 210 preferably has an angular outer surface to facilitate pick up of the flexible carrier 20 and prevent slipping. This preferred shape can be achieved if the pickup spindle 210 has a mainly square cross section, as shown in FIG. 7.

As shown in FIG. 5, the replaceable cartridge 200 is contoured to be inserted into the storage space 240 of the swab dispensing case 230, with the stripping and dispensing chute 90 fitting into the access slot 202 of the replaceable cartridge 200. Properly inserting the replaceable cartridge 200 causes the pickup spindle 210 to engage with the rotating pickup spool 60. When the drive means 80 rotates the rotating pickup spool 60, as described above, the rotating pickup spool 60 causes the pickup spindle 210 to rotate and pull the attached flexible carrier 20 from the storage spool 40 over the support wheel 70 and onto the pickup spindle 210. Properly inserting the replaceable cartridge 200 into the swab dispensing case 230 brings the edge 95 of the stripping and dispensing chute 90 into position at swab dispensing position 75 such that it rips a portion of the continuous strippable attachment means 30 and strips the cotton swabs 10 from the flexible carrier 20 as the flexible carrier 20 moves toward the pickup spindle 210. When the edge 95 strips the cotton swab 10 from the flexible carrier 20, the cotton swab 10 falls into the stripping and dispensing chute 90 and is dispensed to the user. A front panel 276 on the swab dispensing case 230 is preferably transparent; and it preferably has a dispensing case 234, as shown in FIG. 5, for catching the cotton swab 10 as it falls down the stripping and dispensing chute 90. When the replaceable cartridge 200 is inserted into the swab dispensing case 230, the front panel 276 and the front wall 224 are aligned so it is possible to see the storage spool 40 from the outside through both the swab dispensing case 230 and the replaceable cartridge 200.

The replaceable cartridge 200 further includes a disengaging means 278 removably engaging the pickup spindle 210 to the side wall 220 of the replaceable cartridge 200 so as to enable the pickup spindle 210 to rotate freely with the pickup spool 60 once they are engaged. There are many mechanisms which can be used to removably attach the pickup spindle 210 to the side wall 220; however, in its preferred form, the disengaging means 278 is an attachment tab 260 adapted for progressively tearing the pickup spindle 210 away from the side wall 220 of the replaceable cartridge 200. The attachment tab 260 is connected to a attachment ring 262 which is preferably defined by an inner perforation 264 and an outer perforation 266, each of which are coaxial and preferably define larger and smaller concentric circles. The inner perforation 264 defines an inner disk 268 which is the part of the side wall 220 which remains attached to the pickup spindle 210. The side wall 220 between the inner perforation 264 and the outer perforation 266 defines the attachment ring 262. These elements are all preferably circular to facilitate rotation, but other shapes are also possible.

In its preferred embodiment, the swab dispensing case 230 further provides a door 270 for sealing the replaceable cartridge 200 into the swab dispensing case 230. The door 270 is hingedly attached to the swab dispensing case 230 adjacent to the access aperture 250. Once the replaceable cartridge 200 is inserted into the storage space 240 of the swab dispensing case 230, the door 270 can be closed to seal the access aperture 250. The door 270 also preferably has latching means. The preferred latching means is a male contour 272 on the door 270 which removably engages a female contour 274 in the swab dispensing case 230 when the door 270 is closed.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A cotton swab dispensing device providing storage for a supply of cotton swabs, the swabs being interconnected by a flexible carrier including a strippable attachment means for holding the swabs to the carrier, the device comprising:

a storage spool supporting and playing-out a coiled inventory of the cotton swabs mounted on the flexible carrier;

a rotating pickup spool for taking up the flexible carrier as the swabs are dispensed;

a support wheel for supporting a portion of the carrier at a swab dispensing position;

a drive means for rotating the pickup spool for pulling the flexible carrier from the storage spool over the support wheel;

a cotton swab stripping and dispensing chute having an edge positioned such that the edge is wedged between a cotton swab and the flexible carrier in contact with the support wheel, the cotton swab being pulled away from the carrier as the carrier moves toward the pickup spool, the cotton swab thereby breaking the strippable attachment means, and falling into the chute for dispensing.

2. The device of claim 1 wherein the pickup spool provides radially positioned first drive tooth means, and further including a drive sector pivotally mounted and including outwardly extending second drive tooth means, and an idler sprocket, the first and second drive tooth means being positioned for mutual engagement of the idler sprocket such that as the drive sector is moved in pivoted rotational motion, the pickup spool is caused to rotate.

3. The device of claim 2 further including a drive handle mounted and positioned for moving in a pivotal motion for driving the drive sector in pivoted rotational motion.

4. The device of claim 3 further including a pivoted pawl positioned for engaging and alternately disengaging a toothed ratchet means, such that with the pickup spool rotating in a sense for taking up the carrier, the pawl is disengaged therewith, and with the pickup spool tending to rotate in a sense for playing-out the carrier, the pawl engages the toothed ratchet means to lock the pickup spool from rotating.

5. The device of claim 1 further including a housing for enclosing the device such that the cotton swabs are maintained in a sanitary state.

6. The device of claim 5 wherein the housing is made, at least in part, of a transparent material for viewing the cotton swab inventory.

7. A cotton swab dispensing device comprising:

a plurality of cotton swabs, the swabs being interconnected by a flexible carrier including a strippable attachment means for holding the swabs to the carrier as a coiled inventory;

a storage spool supporting and playing-out one of the swabs at a time from the coiled inventory of the cotton swabs mounted on the flexible carrier;

a rotating pickup spool for taking up the flexible carrier as the swabs are dispensed;

a support wheel for supporting a portion of the carrier at a swab dispensing position;

a drive means for rotating the pickup spool for pulling the flexible carrier from the storage spool over the support wheel;

a cotton swab stripping and dispensing chute having an edge positioned such that the edge is wedged between a cotton swab and the flexible carrier in contact with the support wheel the cotton swab being pulled away from the carrier as the carrier moves toward the pickup spool, the cotton swab thereby breaking the strippable attachment means, and falling into the chute for dispensing.

8. The device of claim 7 wherein the pickup spool provides radially positioned first drive tooth means, and further including a drive sector pivotally mounted and including outwardly extending second drive tooth means, and an idler sprocket, the first and second drive tooth means being positioned for mutual engagement of the idler sprocket such that as the drive sector is moved in pivoted rotational motion, the pickup spool is caused to rotate.

9. The device of claim 8 further including a drive handle mounted and positioned for moving in a pivotal motion for driving the drive sector in pivoted rotational motion.

10. The device of claim 8 further including a pivoted pawl positioned for engaging and alternately disengaging a toothed ratchet means, such that with the pickup spool rotating in a sense for taking up the carrier, the pawl is disengaged therewith, and with the pickup spool tending to rotate in a sense for playing-out the carrier, the pawl engages the toothed ratchet means to lock the pickup spool from rotating.

11. The device of claim 7 further including a housing for enclosing the device such that the cotton swabs are maintained in a sanitary state.

12. The device of claim 11 wherein the housing is made, at least in part, of a transparent material for viewing the cotton swab inventory.

13. A cotton swab dispensing device providing storage for a supply of cotton swabs, the swabs being interconnected by a flexible carrier including a strippable attachment means for holding the swabs to the carrier, the device comprising:

a replaceable cartridge providing:
   a storage spool, supporting and playing-out a coiled inventory of the cotton swabs mounted on the flexible carrier;
   a support wheel, supporting a portion of the carrier at a swab dispensing position; and, a pickup spindle removably mounted onto a side wall of the cartridge, the pickup spindle enabling the winding-up of the flexible carrier as the swabs are dispensed;

a swab dispensing case providing:
   a storage space for holding the cartridge;
   an access aperture for inserting and removing the cartridge, into and out of the storage space respectively;
   a rotating pickup spool engagable with the pickup spindle for rotation thereof;
   a drive means for rotating the pickup spool for pulling the flexible carrier from the storage spool over the support wheel; and
   a cotton swab stripping and dispensing chute having an edge positioned such that the edge is wedged between each of the cotton swabs in turn, whereby each of the cotton swabs, in turn, is pulled away from the carrier as the carrier moves toward the pickup spool, the cotton swab thereby breaking the strippable attachment means, so as to fall into the chute for dispensing;

a means for disengaging the pickup spindle from the side wall of the cartridge so as to enable the pickup spindle to rotate freely with the pickup spool.

14. The device of claim 13 wherein the disengaging means is an attachment tab adapted for progressively tearing the pickup spindle away from the sidewall of the cartridge.

15. The device of claim 13 wherein the swab dispensing case provides a door for sealing the cartridge into the dispensing case.

16. The device of claim 13 wherein the pickup spindle defines a hollow space therewithin, the pickup spool being engaged within the pickup spindle such that rotation of the pickup spool causes the pickup spindle to rotate therewith.

* * * * *